(12) United States Patent
Taylor et al.

(10) Patent No.: US 8,147,853 B2
(45) Date of Patent: Apr. 3, 2012

(54) PERSONAL CARE COMPOSITIONS CONTAINING HYDROPHOBICALLY MODIFIED NON-PLATELET PARTICLES

(75) Inventors: Rebecca Ann Taylor, Cincinnati, OH (US); Mannie Lee Clapp, Mason, OH (US); Qing Stella, Cincinnati, OH (US); John Christopher Wesner, Liberty Township, OH (US); Cynthia Ann Garza, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 131 days.

(21) Appl. No.: 11/057,957

(22) Filed: Feb. 15, 2005

(65) Prior Publication Data
US 2006/0182699 A1 Aug. 17, 2006

(51) Int. Cl.
*A61K 8/18* (2006.01)
(52) U.S. Cl. ........................................ 424/401
(58) Field of Classification Search .................. None
See application file for complete search history.

(56) References Cited

U.S. PATENT DOCUMENTS

| | | |
|---|---|---|
| 1,985,424 A | 12/1934 | Piggott |
| 2,438,091 A | 3/1948 | Lynch |
| 2,528,378 A | 10/1950 | Mannheimer |
| 2,658,072 A | 11/1953 | Kosmin |
| 2,703,798 A | 3/1955 | Schwartz |
| 2,965,576 A | 12/1960 | Wilson |
| 3,087,829 A | 4/1963 | Linton et al. |
| 3,123,490 A | 3/1964 | Bolomey et al. |
| 3,892,881 A | 7/1975 | Lissant |
| 4,323,544 A | 4/1982 | Magder |
| 4,389,418 A | 6/1983 | Burton |
| 4,606,913 A | 8/1986 | Aronson et al. |
| 4,832,858 A | 5/1989 | Vishnupad et al. |
| 4,956,170 A | 9/1990 | Lee |
| 4,970,252 A | 11/1990 | Sakuta et al. |
| 4,980,155 A | 12/1990 | Shah et al. |
| 4,981,677 A | 1/1991 | Thau |
| 4,999,186 A | 3/1991 | Sabatelli et al. |
| 5,002,680 A | 3/1991 | Schmidt et al. |
| 5,004,598 A | 4/1991 | Lochhead et al. |
| 5,035,890 A | 7/1991 | Braun |
| 5,223,559 A | 6/1993 | Arraudeau et al. |
| 5,228,912 A | 7/1993 | Herget et al. |
| 5,290,471 A | 3/1994 | Greene et al. |
| 5,304,334 A | 4/1994 | Lahanas et al. |
| 5,364,617 A | 11/1994 | Bush et al. |
| 5,387,417 A | 2/1995 | Rentsch |
| 5,462,963 A | 10/1995 | Bush et al. |
| 5,472,728 A | 12/1995 | Miller et al. |
| 5,487,168 A | 1/1996 | Geiner et al. |
| 5,487,884 A | 1/1996 | Bissett et al. |
| 5,490,995 A | 2/1996 | Corrigan |
| 5,534,265 A | 7/1996 | Fowler et al. |
| 5,540,853 A | 7/1996 | Trinh et al. |
| 5,556,628 A | 9/1996 | Derian et al. |
| 5,578,299 A | 11/1996 | Starch |
| 5,607,980 A | 3/1997 | McAtee et al. |
| 5,612,307 A | 3/1997 | Chambers et al. |
| 5,618,522 A | 4/1997 | Kaleta et al. |
| 5,635,171 A | 6/1997 | Nadaud |
| 5,652,228 A | 7/1997 | Bissett |
| 5,654,362 A | 8/1997 | Schulz, Jr. et al. |
| 5,661,189 A | 8/1997 | Grievson et al. |
| 5,667,800 A | 9/1997 | De Vringer |
| 5,674,511 A | 10/1997 | Kacher et al. |
| 5,681,852 A | 10/1997 | Bissett |
| 5,686,082 A | 11/1997 | Nguyen |
| 5,686,087 A | 11/1997 | Ansmann et al. |
| 5,687,779 A | 11/1997 | Andersson et al. |
| 5,716,920 A | 2/1998 | Glenn et al. |
| 5,747,011 A | 5/1998 | Ross et al. |
| 5,760,116 A | 6/1998 | Kilgour et al. |
| 5,811,487 A | 9/1998 | Schulz, Jr. et al. |
| 5,817,609 A | 10/1998 | He et al. |
| 5,849,281 A | 12/1998 | Babinski et al. |
| 5,851,978 A | 12/1998 | Shana'a |
| 5,869,071 A | 2/1999 | Wieselman et al. |
| 5,873,494 A | 2/1999 | Dallas, Jr. |
| 5,885,342 A | 3/1999 | Gale et al. |
| 5,885,948 A | 3/1999 | Glenn, Jr. et al. |
| 5,888,492 A | 3/1999 | Starch |
| 5,914,117 A | 6/1999 | Lavaud |
| 5,914,177 A | 6/1999 | Smith, III |
| 5,925,603 A | 7/1999 | D'Angelo |
| 5,928,632 A | 7/1999 | Reusch |
| 5,929,019 A | 7/1999 | Puvvada et al. |
| 5,948,417 A * | 9/1999 | Mori .............................. 424/401 |

(Continued)

FOREIGN PATENT DOCUMENTS

CA 2246316 6/1998

(Continued)

OTHER PUBLICATIONS

Emmert, Dr. Ralf, "Quantification of the Soft-Focus Effect", Cosmetics & Toiletries, vol. 111, pp. 57-61 (Jul. 1996).
Treated Pigments—KOBO Technical Brochure, XP002299173 (May 2000) http://www.koboproductsinc.com/Downloads/TreatedPigments.pdf.
Special Effects Pigments—KOBO, XP002299376 (Jul. 24, 2003) http://www.koboproductsinc.com/SEP.html.
C.D. Vaughan, "Solubility Effects in Product, Package, Penetration and Preservation," Cosmetic and Toiletries, vol. 103, Oct. 1988.
C.D. Vaughn, "Using Solubility Parameters in Cosmetics Formulations," 36 J. Soc. Cosmetic Chemists 319-333, Sep./Oct. 1988.
C.J. van Oss, "Coacervation, Complex-Coacervation and Flocculation," J. Dispersion Science and Technology, vol. 9 (5,6), 1988-89, P 561-573.

(Continued)

*Primary Examiner* — Anand Desai
*Assistant Examiner* — Melissa S Mercier

(57) ABSTRACT

A rinsable personal care composition includes (a) 0 to 75 weight percent of a composition surfactant; (b) 0.01 to 99 weight percent of a skin benefit agent or emollient; (c) 0.01 to 20 weight percent of a hydrophobically modified non-platelet particle; and (d) 0 to 99% water.

23 Claims, No Drawings

U.S. PATENT DOCUMENTS

| | | | |
|---|---|---|---|
| 5,952,286 A | 9/1999 | Puvvada et al. | |
| 5,954,213 A | 9/1999 | Gerhart et al. | |
| 5,965,500 A | 10/1999 | Puvvada | |
| 5,965,501 A | 10/1999 | Rattinger et al. | |
| 5,972,361 A | 10/1999 | Fowler et al. | |
| 5,977,188 A | 11/1999 | Okamoto et al. | |
| 5,989,536 A | 11/1999 | Deckner et al. | |
| 6,001,373 A * | 12/1999 | Igo-Kemenes et al. | 424/401 |
| 6,068,834 A | 5/2000 | Kvalnes et al. | |
| 6,132,873 A | 10/2000 | Dietz et al. | |
| 6,150,403 A | 11/2000 | Biedermann et al. | |
| 6,174,533 B1 | 1/2001 | SaNogueira, Jr. et al. | |
| 6,183,766 B1 | 2/2001 | Sine et al. | |
| 6,190,648 B1 | 2/2001 | Kouzu et al. | |
| 6,194,364 B1 | 2/2001 | Glenn, Jr. | |
| 6,217,888 B1 | 4/2001 | Oblong et al. | |
| 6,232,496 B1 | 5/2001 | Carr et al. | |
| 6,245,323 B1 | 6/2001 | Christie et al. | |
| 6,261,541 B1 | 7/2001 | Karpov et al. | |
| 6,280,757 B1 | 8/2001 | McAtee et al. | |
| 6,290,936 B1 | 9/2001 | Ross et al. | |
| 6,335,312 B1 | 1/2002 | Coffindaffer et al. | |
| 6,340,723 B1 | 1/2002 | Nita et al. | |
| 6,342,208 B1 | 1/2002 | Hyldgaard et al. | |
| 6,355,230 B2 | 3/2002 | Gers-Barlag et al. | |
| 6,361,781 B2 | 3/2002 | Lorant | |
| 6,367,519 B2 | 4/2002 | Thibiant et al. | |
| 6,385,992 B1 | 5/2002 | Flore, Jr. | |
| 6,394,323 B2 | 5/2002 | McClean et al. | |
| 6,395,690 B1 | 5/2002 | Tsaur | |
| 6,395,691 B1 | 5/2002 | Tsaur | |
| 6,410,035 B1 | 6/2002 | Gers-Barlag et al. | |
| 6,419,783 B1 | 7/2002 | Rainey et al. | |
| 6,419,938 B1 | 7/2002 | Riedel et al. | |
| 6,426,326 B1 | 7/2002 | Mitra et al. | |
| 6,429,177 B1 | 8/2002 | Williams et al. | |
| 6,471,762 B1 | 10/2002 | DeLuca, Jr. et al. | |
| 6,491,932 B1 | 12/2002 | Ramin et al. | |
| 6,495,498 B2 | 12/2002 | Niemiec et al. | |
| 6,506,391 B1 | 1/2003 | Biatry | |
| 6,516,838 B2 | 2/2003 | Biatry | |
| 6,517,939 B1 | 2/2003 | Ramin et al. | |
| 6,521,216 B1 | 2/2003 | Glandorf et al. | |
| 6,534,456 B2 | 3/2003 | Hayward et al. | |
| 6,534,457 B2 | 3/2003 | Shuman et al. | |
| 6,534,458 B1 | 3/2003 | Hayward et al. | |
| 6,545,085 B2 | 4/2003 | Kilgour et al. | |
| 6,547,063 B1 | 4/2003 | Zaveri et al. | |
| 6,548,629 B2 | 4/2003 | Kilgour et al. | |
| 6,555,509 B2 | 4/2003 | Abbas et al. | |
| 6,564,978 B1 | 5/2003 | Safian et al. | |
| 6,574,985 B2 | 6/2003 | Fiore, Jr. | |
| 6,576,623 B1 | 6/2003 | Nakanish | |
| 6,579,529 B2 | 6/2003 | Gers-Barlag et al. | |
| 6,589,509 B2 | 7/2003 | Keller et al. | |
| 6,620,420 B2 | 9/2003 | Lanzendorfer | |
| 6,645,511 B2 * | 11/2003 | Aronson et al. | 424/401 |
| 6,648,176 B1 | 11/2003 | Donovan | |
| 6,652,134 B2 | 11/2003 | Lloyd | |
| 6,663,855 B2 | 12/2003 | Frechet et al. | |
| 6,664,217 B1 | 12/2003 | Puvvada et al. | |
| 6,673,280 B1 | 1/2004 | Yang | |
| 6,673,371 B2 | 1/2004 | Brown et al. | |
| 6,673,755 B2 | 1/2004 | Wei et al. | |
| 6,691,394 B1 | 2/2004 | McClean | |
| 6,695,510 B1 | 2/2004 | Look et al. | |
| 6,699,488 B2 | 3/2004 | Deckner et al. | |
| 6,703,029 B1 | 3/2004 | Gers-Barlag et al. | |
| 6,709,662 B1 | 3/2004 | Gers-Barlag et al. | |
| 6,716,440 B2 | 4/2004 | Aronson et al. | |
| 6,723,688 B1 | 4/2004 | Malik et al. | |
| 6,727,209 B2 | 4/2004 | Pereira et al. | |
| 6,752,982 B2 | 6/2004 | Colwell et al. | |
| 6,759,376 B2 | 7/2004 | Zhang et al. | |
| 6,780,826 B2 * | 8/2004 | Zhang et al. | 510/130 |
| 6,797,742 B2 | 9/2004 | Kilgour et al. | |
| 6,803,049 B2 | 10/2004 | Gers-Barlag et al. | |
| 6,808,722 B2 * | 10/2004 | Victor | 424/489 |
| 6,923,975 B2 | 8/2005 | Aronson et al. | |
| 6,924,256 B2 | 8/2005 | Massaro et al. | |
| 7,056,914 B2 | 6/2006 | Jover et al. | |
| 7,192,598 B2 | 3/2007 | Aronson et al. | |
| 7,204,975 B2 | 4/2007 | Gers-Barlag et al. | |
| 7,229,486 B2 | 6/2007 | Wiersema et al. | |
| 7,268,104 B2 | 9/2007 | Krzysik et al. | |
| 7,273,837 B2 | 9/2007 | Boutique et al. | |
| 7,511,003 B2 | 3/2009 | Focht et al. | |
| 7,524,807 B2 | 4/2009 | Clapp et al. | |
| 7,560,125 B2 | 7/2009 | Ananthapadmanabhan et al. | |
| 7,666,825 B2 | 2/2010 | Wagner et al. | |
| 7,776,346 B2 | 8/2010 | O'Connor et al. | |
| 7,776,347 B2 | 8/2010 | Kerschner et al. | |
| 7,838,479 B2 | 11/2010 | Mitra et al. | |
| 7,867,962 B2 | 1/2011 | Wei et al. | |
| 7,875,582 B2 | 1/2011 | Pham et al. | |
| 2001/0006088 A1 | 7/2001 | Lyle | |
| 2001/0022966 A1 | 9/2001 | Gers-Barlag et al. | |
| 2001/0047039 A1 | 11/2001 | McManus et al. | |
| 2002/0018789 A1 | 2/2002 | Gers-Barlag et al. | |
| 2002/0022007 A1 | 2/2002 | Gers-Barlag et al. | |
| 2002/0022040 A1 | 2/2002 | Robinson et al. | |
| 2002/0082745 A1 | 6/2002 | Wilmott et al. | |
| 2002/0119111 A1 | 8/2002 | Kilgour et al. | |
| 2003/0003069 A1 | 1/2003 | Carson et al. | |
| 2003/0049282 A1 | 3/2003 | Aronson et al. | |
| 2003/0054019 A1 | 3/2003 | Aronson et al. | |
| 2003/0072827 A1 | 4/2003 | Steenbergen | |
| 2003/0152540 A1 | 8/2003 | Putman et al. | |
| 2003/0161805 A1 | 8/2003 | Schlossman et al. | |
| 2003/0161852 A1 | 8/2003 | Miller et al. | |
| 2003/0180246 A1 | 9/2003 | Frantz et al. | |
| 2003/0190336 A1 | 10/2003 | Adams et al. | |
| 2003/0222100 A1 | 12/2003 | Husband et al. | |
| 2004/0005285 A1 | 1/2004 | Midha | |
| 2004/0048757 A1 | 3/2004 | Zhang et al. | |
| 2004/0048758 A1 | 3/2004 | Zhang et al. | |
| 2004/0057920 A1 | 3/2004 | Focht et al. | |
| 2004/0081679 A1 | 4/2004 | Simon et al. | |
| 2004/0091445 A1 | 5/2004 | Dykstra et al. | |
| 2004/0092415 A1 | 5/2004 | Focht et al. | |
| 2004/0105827 A1 | 6/2004 | Grimm et al. | |
| 2004/0146475 A1 | 7/2004 | Peffly et al. | |
| 2004/0158940 A1 | 8/2004 | Wells et al. | |
| 2004/0180020 A1 | 9/2004 | Manelski et al. | |
| 2004/0219119 A1 | 11/2004 | Wei et al. | |
| 2004/0223929 A1 | 11/2004 | Clapp et al. | |
| 2004/0223939 A1 | 11/2004 | Clausen et al. | |
| 2004/0223991 A1 * | 11/2004 | Wei et al. | 424/401 |
| 2004/0223992 A1 | 11/2004 | Clapp et al. | |
| 2004/0223993 A1 | 11/2004 | Clapp et al. | |
| 2004/0232023 A1 | 11/2004 | Bansal et al. | |
| 2004/0234468 A1 | 11/2004 | Kerschner et al. | |
| 2004/0234469 A1 | 11/2004 | O'Connor et al. | |
| 2004/0234470 A1 | 11/2004 | Zhang et al. | |
| 2004/0234477 A1 | 11/2004 | Sakuta | |
| 2004/0234478 A1 | 11/2004 | Clapp et al. | |
| 2004/0234558 A1 | 11/2004 | O'Connor et al. | |
| 2004/0234565 A1 | 11/2004 | Stella et al. | |
| 2004/0235691 A1 | 11/2004 | Pham et al. | |
| 2004/0242706 A1 | 12/2004 | Wiersema et al. | |
| 2004/0248748 A1 | 12/2004 | Wei et al. | |
| 2005/0003975 A1 | 1/2005 | Browne et al. | |
| 2005/0020468 A1 | 1/2005 | Frantz et al. | |
| 2005/0100570 A1 | 5/2005 | Wei et al. | |
| 2005/0143269 A1 | 6/2005 | Wei et al. | |
| 2005/0192187 A1 | 9/2005 | Wagner et al. | |
| 2005/0192189 A1 | 9/2005 | Wagner et al. | |
| 2005/0238680 A1 | 10/2005 | Stella et al. | |
| 2005/0249758 A1 | 11/2005 | Di Puccio Pagano | |
| 2005/0250658 A1 | 11/2005 | Putman et al. | |
| 2005/0276768 A1 | 12/2005 | Wei et al. | |
| 2006/0002880 A1 | 1/2006 | Peffly et al. | |
| 2006/0008438 A1 | 1/2006 | Velarde et al. | |
| 2006/0079420 A1 | 4/2006 | Wagner et al. | |
| 2006/0079421 A1 | 4/2006 | Wagner et al. | |
| 2006/0094628 A1 | 5/2006 | Wei et al. | |
| 2006/0210505 A1 | 9/2006 | Clapp et al. | |

| | | | |
|---|---|---|---|
| 2006/0239953 A1 | 10/2006 | Clapp et al. | |
| 2007/0293411 A1 | 12/2007 | Focht et al. | |
| 2008/0039353 A1 | 2/2008 | Focht et al. | |
| 2008/0045428 A1 | 2/2008 | Focht et al. | |
| 2008/0045429 A1 | 2/2008 | Focht et al. | |

FOREIGN PATENT DOCUMENTS

| | | |
|---|---|---|
| CA | 2300227 | 9/2001 |
| DE | 10 2004/045253 A1 | 4/2006 |
| EP | 0 078 138 B1 | 5/1983 |
| EP | 0 398409 B1 | 11/1990 |
| EP | 0 917870 A1 | 5/1999 |
| EP | 1 005849 A1 | 6/2000 |
| EP | 1 097695 A1 | 5/2001 |
| EP | 1064918 B1 | 9/2002 |
| EP | 1 360955 A2 | 11/2003 |
| FR | 2843540 A1 | 2/2004 |
| FR | 2843541 A1 | 2/2004 |
| FR | 2863873 A1 | 6/2005 |
| JP | 8 0999855 A | 4/1996 |
| JP | 8 151313 A | 6/1996 |
| JP | 08188723 | 7/1996 |
| JP | 11193215 | 7/1999 |
| JP | 2000 229817 A | 8/2000 |
| JP | 2000 351993 A | 12/2000 |
| JP | 2001 278731 A | 10/2001 |
| JP | 2002-128639 A | 5/2002 |
| JP | 2002-138010 A | 5/2002 |
| JP | 2002 275022 A | 9/2002 |
| WO | WO 94/10973 A1 | 5/1994 |
| WO | WO 95/26710 A | 10/1995 |
| WO | WO 95/34280 | 12/1995 |
| WO | WO 97/17938 A | 5/1997 |
| WO | WO 98/27193 A1 | 6/1998 |
| WO | WO 98/50471 A | 11/1998 |
| WO | WO 99/24001 A1 | 5/1999 |
| WO | WO 99/38489 A1 | 8/1999 |
| WO | WO 99/38491 A1 | 8/1999 |
| WO | WO 00/75240 A1 | 12/2000 |
| WO | WO 0108644 A1 | 2/2001 |
| WO | WO 01/70270 A2 | 9/2001 |
| WO | WO 01/74979 A1 | 10/2001 |
| WO | WO 01/76543 A1 | 10/2001 |
| WO | WO 02/067888 A1 | 9/2002 |
| WO | WO 02/100358 A1 | 12/2002 |
| WO | WO 2004065536 A1 | 8/2004 |
| WO | WO 2006021350 A1 | 3/2006 |

OTHER PUBLICATIONS

Crank, Mathematics of Diffusion, $2^{nd}$ Edition, pp. 63 (1975).
CTFA International Cosmetic Ingredient Dictionary, Fourth Edition, 1991, pp. 12 and 80.
D.J. Burgess, "Practical Analysis of Complex Coacervate Systems," J. of Collois Anti Interface Science, vol. 40, No. 1, Nov. 1990, pp. 227-238.
Emmert, Dr. Ralf, "Quantfication of the Soft-Focus Effect," Cosmetics & Toiletries, vol. 111, pp. 57-61 (Jul. 1996).
J. Caelles et al., "Anionic and Cationic Compounds in Mixed Systems", Cosmetics & Toiletries, vol. 106, Apr. 1991, pp. 49-54.
Special Effects Pigments—KOBO, XP002299376 (Jul. 24, 2003) Online URL:http://www.koboproductsinc.com/SEP.html.
Treated Pigments—KOBO Technical Brochure, XP002299173 (May 2000) Online URL:http://www.koboproductsinc.com/Downloads/TreatedPigments.pdf.
XP002332778 "Dove All Day Moisturizing Body Wash" Online URL:http://www.ewg.org/reports/skindeep2/report.php?type=PRODUCT&id=8801874 accessed Feb. 8, 2006.
XP002332779 "Olay Daily Renewal Moisturizing Body Wash" Online URL:http://householdproducts.nlm.nih.gov/cgi-bin/household.brands?tbl=brands&id=16003084 accesses Feb, 8, 2006.

* cited by examiner

PERSONAL CARE COMPOSITIONS CONTAINING HYDROPHOBICALLY MODIFIED NON-PLATELET PARTICLES

FIELD OF THE INVENTION

The present invention relates to the field of personal care compositions for improving appearance and feel of keratinous surfaces. More specifically, the present invention relates to rinsable personal care compositions that provide excellent skin appearance, skin moisturization and conditioning.

BACKGROUND OF THE INVENTION

Personal care compositions are well known and widely used. These compositions have long been employed to cleanse and moisturize skin, deliver actives, hide imperfections and to reduce the oiliness/shine associated with sebum. Personal care compositions have also been used to alter the color and appearance of skin.

These compositions generally incorporate organic or inorganic particulate material to reduce the shine or redness of skin, to also cover over skin imperfections such as wrinkles, and even to provide cosmetic effects such as whitening or darkening. For example, the use of TiO2 as a skin whitening agent has been known since ancient times, and the formulator's chemical library is replete with pigments which can be blended to produce an almost arbitrary range of colors to skin. Other particles, such as silicas and silicone resins can produce a mattifying effect on skin, reducing the appearance of fine lines and wrinkles.

Recently, advances have been disclosed in the art in depositing from rinse-off products a specific class of effect particles based on a platelet shape. When particles are present as platelets, they produce a higher degree of specular reflectance and tend to lend a shiny appearance to skin. While this may often be desired, it is also desirable to provide visual benefits to skin from particles that are non-platelet in shape, that do not have a shiny appearance on the skin surface.

While the compositions and disclosures of the prior art provide useful advances in the art of personal care compositions, there remains the need for improved rinse off compositions that deliver immediate improvements in appearance and skin feel that will effectively deposit on all parts of the body. The compositions also need to be non-greasy and easy to apply. Therefore, it is desirable to provide a topical rinse off composition comprising a select level and blend of non-platelet particles to provide a unique level of skin appearance change across all skin types. It is also desirable to provide personal care compositions that effectively provide skin moisturization. It is further desirable to deliver the above skin conditioning and appearance benefits via an in-the-shower or in-the-bath lotion. Unfortunately, in the shower/bath, moisturizers are often readily rinsed from the skin. This is particularly true when surfactant is present. Therefore a need still exists for compositions that can effectively deposit appearance and skin feel particles in a rinse-off environment.

SUMMARY OF THE INVENTION

The present invention relates to a rinsable personal care composition comprises (a) 0 to 75 weight percent of a composition surfactant; (b) 0.01 to 99 weight percent of a skin benefit agent or emollient; (c) 0.01 to 20 weight percent of a hydrophobically modified non-platelet particle; and (d) 0 to 99% water.

DETAILED DESCRIPTION OF THE INVENTION

All percentages and ratios used herein are by weight of the total composition and all measurements made are at 25° C., unless otherwise designated.

The term "amphoteric surfactant," as used herein, is also intended to encompass zwitterionic surfactants, which are well known to formulators skilled in the art as a subset of amphoteric surfactants.

The term "dermatologically-acceptable," as used herein, means that the compositions or components thereof so described are suitable for use in contact with human skin without undue toxicity, incompatibility, instability, allergic response, and the like.

The term "diameter" as used herein, means the largest distance across the major axis of the particulate material. Diameter can be determined by any suitable method known in the art, such as particle size analyzer Mastersizer 2000 manufactured by Malvern Instruments.

The term "gel-network" as used herein, means an emulsifying system comprised of fatty alcohol and a hydrophilic surfactant.

The term "hydrophobically modified interference pigment" or "HMIP", as used herein, means a portion of the interference pigment surface has been coated with a hydrophobic material.

The term "interference pigment", as used herein, means a pigment with pearl gloss prepared by coating the surface of a particle substrate material (generally platelet in shape) with a thin film. The thin film is a transparent or semitransparent material having a high refractive index. The higher refractive index material shows a pearl gloss resulting from mutual interfering action between reflection and incident light from the platelet substrate/coating layer interface and reflection of incident light from the surface of the coating layer.

As used, herein "Non-platelet particle," refers to any shape of a particle in the personal care composition differing from the platelet shape including configurations but not limited to spherical, cylindrical configuration, rectangular, triangular, trapezoidal, semi-circular, hourglass, or irregular shapes. The non-platlet particles may have an aspect ratio define by A/B=or >0.20, the length A and the width being B, more preferably greater than 0.25, even more preferably greater than 0.3

The term, "personal care composition" as used herein refers to unless otherwise specified, refers to the compositions of the present invention, wherein the compositions are intended to include compositions for topical application to the skin or hair.

The term "rinsable composition" as used herein, means a composition designed to be rinsed off by a liquid such as water. After the composition is rinsed off, pigments are deposited on the skin and the skin radiance is realized.

The term "safe and effective amount" as used herein means an amount of a compound, component, or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound medical judgment.

A "skin compatible oil" as defined herein, is an oil that is liquid or semi-solid at the temperature at which bathing is carried out that is deemed safe for use in cosmetics being either inert to the skin or actually beneficial.

The term "topical application", as used herein, means to apply or spread the compositions of the present invention onto the surface of the skin.

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

A. Composition Surfactant

The rinsable personal care composition of the present invention comprises 0 to 75 weight percent of a composition surfactant. A wide variety of composition surfactants can be useful herein, both for emulsification of the dispersed phase as well as to provide acceptable spreading and in use properties for non-lathering systems. For cleansing applications, the surfactant phase also serves to clean the skin and provide an acceptable amount of lather for the user. The composition preferably contains no more than about 50 weight percent of a surfactant, more preferably no more than about 30 weight percent, still more preferably no more than about 15 weight percent, and even more preferably no more than about 5 weight percent of a surfactant. The composition preferably contains at least about 5 weight percent of a surfactant, more preferably at least about 3 weight percent, still more preferably at least about 1 weight percent, and even more preferably at least about 0.1 weight percent of a surfactant. For cleansing applications the personal care compositions preferably produces a Total Lather Volume of at least 300 ml, more preferably greater than 600 ml as described in the Lathering Volume Test. The personal care compositions preferably produces a Flash Lather Volume of at least 100 ml, preferably greater than 200 ml, more preferably greater than 300 ml as described in the Lathering Volume Test.

Preferable surfactants include those selected from the group consisting of anionic surfactants, nonionic surfactants, amphoteric surfactants, non-lathering surfactants, emulsifiers and mixtures thereof. Non-limiting examples of surfactants useful in the compositions of the present invention are disclosed in U.S. Pat. No. 6,280,757, to McAtee et al., issued Aug. 28, 2001.

a. Anionic Surfactants

Non-limiting examples of anionic surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975.

A wide variety of anionic surfactants are useful herein. Non-limiting examples of anionic surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are fatty acid soaps (i.e., alkali metal salts, e.g., sodium or potassium salts) typically having from a fatty acid having about 8 to about 24 carbon atoms, preferably from about 10 to about 20 carbon atoms. These fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853.

Other anionic materials include phosphates such as monoalkyl, dialkyl, and trialkylphosphate salts. Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein is ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

b. Non-ionic Surfactants

Non-limiting examples of nonionic surfactants for use in the compositions of the present invention are disclosed in McCutcheon's, Detergents and Emulsifiers, North American edition (1986), published by allured Publishing Corporation; and McCutcheon's, Functional Materials, North American Edition (1992).

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Non-limiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, lauramine oxide, cocoamine oxide and mixtures thereof.

c. Amphoteric Surfactants

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992).

Non-limiting examples zwitterionic surfactants are those selected from the group consisting of betaines, sultaines, hydroxysultaines, alkyliminoacetates, iminodialkanoates, aminoalkanoates, and mixtures thereof.

Preferred surfactants for use herein are the following, wherein the anionic surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the non-ionic surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

d. Non-Lathering Surfactants

A wide variety of non-lathering surfactants are useful herein. The composition of the present invention can comprise a sufficient amount of one or more non-lathering surfactants to emulsify the dispersed phase to yield an appropriate particle size and good application properties on wet skin.

Nonlimiting examples of these non-lathering compositions are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

e. Emulsifier Systems

In addition, there are several commercial emulsifier mixtures that are useful in some embodiments. Examples include but are not limited to PROLIPID 141 (glyceryl stearate, behenyl alcohol, palmitic acid, stearic acid, lecithin, lauryl alcohol, myristyl alcohol and cetyl alcohol) and 151 (Glyceryl stearate, cetearyl alcohol, stearic acid, 1-propanamium, 3-amino-N-(2-(hydroxyethyl)-N—N-Dimethyl, N-C(16-18) Acyl Derivatives, Chlorides) from ISP; POLAWAX NF (Emulsifying wax NF), INCROQUAT BEHENYL TMS (behentrimonium sulfate and cetearyl alcohol) from Croda; and EMULLIUM DELTA (cetyl alcohol, glyceryl stearate, peg-75 stearate, ceteth-20 and steareth-20) from Gattefosse. The emulsifier systems used in conjunction with the present invention should not be limited to those disclosed in the specification, one skilled could use any emulsifier system know in the art keeping in mind the personal care composition of the present invention.

B. Skin Benefit Agent or Emollient

The compositions of the present invention comprise 0.01 to 99 weight percent of a skin benefit agent or emollient. The skin benefit agent or emollient comprises a skin compatible oil, gel, or wax, or mixtures thereof. By definition, the skin benefit agent or emollient will have negligible solubility in any aqueous phase and may be present as discrete particles in the composition. The skin benefit agent or emollient preferably comprises no more than about 99 weight percent of the composition, more preferably no more than about 70 weight percent, still more preferably no more than about 60 weight percent, and still more preferably no more than about 50 weight percent of the composition. The skin benefit agent or emollient preferably comprises at least about 0.01 weight percent, more preferably at least about 5 weight percent, even more preferably at least about 7 weight percent, and still more preferably at least 10% of the composition.

The shear index is a measure of how shear thinning the materials are as described in the Lipid Rheology method described herein. It is preferred that the skin compatible oil be shear thinning either by virtue of its composition or the structurants that may be added. Preferably, the shear index of the skin benefit agent or emollient will preferably be less than 0.9, more preferably less than 0.75, even more preferably less than 0.6, even more preferably less than 0.5, and still more preferably less than 0.4.

The most useful skin compatible oils for the present invention include ester oils, hydrocarbon oils, and silicone oils.

Ester oils, as the name implies, have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, diisopropyl sebacate, diisostearyl malate, isostearyl neopentanoate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like.

A second type of useful ester oil is predominantly comprised of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed. Modified triglycerides include materials such as ethoxylated and maleated triglyceride derivatives provided they are liquids. Proprietary ester blends such as those sold by Finetex as Finsolv are also suitable, as is ethylhexanoic acid glyceride.

A third type of ester oil is liquid polyester formed from the reaction of a dicarboxylic acid and a diol. Examples of polyesters suitable for the present invention are the polyesters marketed by ExxonMobil under the trade name PURESYN ESTER®.

A second class of skin compatible oils suitable for the present invention is liquid and semi-solid hydrocarbons. These include linear and branched oils such as liquid paraffin, squalene, squalane, mineral oil, low viscosity synthetic hydrocarbons such as polyalphaolefin sold by ExxonMobil under the trade name of PURESYN PAO and polybutene under the trade name PANALANE or INDOPOL. Light (low viscosity) highly branched hydrocarbon oils are also suitable.

Petrolatum is a unique hydrocarbon material and a useful component of the present invention. Its semi-solid nature can be controlled both in production and by the formulator through blending with other oils.

A third class of useful skin compatible oils is silicone based. They include linear and cyclic polydimethyl siloxane, organo functional silicones (alkyl and alkyl aryl), and amino silicones.

The personal care compositions of the present invention may optionally further comprise a skin benefit agent suitable for use on the skin, and which is otherwise compatible with the other selected ingredients in the composition. The skin benefit agent can be blended with the oils previously described and included as part of the main high internal phase emulsion. In this case the oil functions as a carrier for the skin benefit agent. The skin benefit agent may also be included as part of a separate high internal phase emulsion. The skin benefit agent may also be included as an add-on ingredient wherein it is not part of any of the high internal phase emulsion premixes.

Non-limiting examples of skin benefit agents suitable for use herein are described in The CTFA Cosmetic Ingredient Handbook, Second Edition (1992), which includes a wide variety of cosmetic and pharmaceutical ingredients commonly used in the skin care industry, and which are suitable for use in the compositions of the present invention. Non-limiting examples of such skin benefit agents include abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antimicrobial agents (e.g., iodopropyl butylcarbamate), antioxidants, colorants, cosmetic astringents, cosmetic biocides, drug astringents, external analgesics, opacifying agents, pH adjusters, skin bleaching and lightening agents (e.g., hydroquinone, kojic acid, ascorbic acid, magnesium ascorbyl phosphate, ascorbyl glucosamine), skin-conditioning and/or moisturizing agents, i.e. glycerine and other humectants, skin soothing and/or healing agents (e.g., panthenol and derivatives (e.g., ethyl panthenol), aloe vera, pantothenic acid and its derivatives, allantoin, bisabolol, and dipotassium glycyrrhizinate), retinoids, (e.g. retinol palmitate), tocopheryl nicotinate, skin treating agents, vitamins and derivatives thereof. In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed. The skin benefit agents are furthered described hereinafter in details.

A) Desquamation Actives

The skin benefit agent for use herein can include desquamation actives, preferred concentrations of which range from about 0.1% to about 10%, more preferably from about 0.2% to about 5%, even more preferably from about 0.5% to about 4%, by weight of the composition for non-surfactant containing actives and from about 0.1% to about 3%, more preferably from about 0.2% to about 3%, even more preferably from about 0.5% to about 3% for surfactant containing actives. Desquamation actives enhance the skin appearance benefits of the present invention. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett.

Another desquamation system that is suitable for use herein contains salicylic acid and zwitterionic surfactants and is described in U.S. Pat. No. 5,652,228 to Bissett.

B) Anti-Acne Actives

The skin benefit agent for use herein can also include anti-acne actives, preferred concentrations of which range from about 0.01% to about 50%, more preferably from about 1% to about 20%, by weight of the composition. Non-limiting examples of anti-acne actives suitable for use herein include resorcinol, sulfur, salicylic acid, benzoyl peroxide, erythromycin, zinc, and other similar materials.

Other non-limiting examples of suitable anti-acne actives for use herein are described in U.S. Pat. No. 5,607,980, issued to McAtee et al, which description is incorporated herein by reference.

C) Anti-Wrinkle Actives/Anti-Atrophy Actives

The skin benefit agent for use herein can also include anti-wrinkle actives or anti-atrophy actives, including sulfur-containing D and L amino acids and their derivatives and salts, particularly the N-acetyl derivatives, a preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, and skin peel agents (e.g., phenol and the like). Also suitable is niacinamide.

Hydroxy acids as skin benefit agents herein include salicylic acid and salicylic acid derivatives, preferred concentrations of which range from about 0.01% to about 50%, more preferably from about 0.1% to about 10%, even more preferably from about 0.5% to about 2%, by weight of the composition.

Other non-limiting examples of suitable anti-wrinkle actives for use herein are described in U.S. Pat. No. 6,217,888, issued to Oblong et al.

D) Anti-Oxidants/Radical Scavengers

The skin benefit agent for use herein can also include anti-oxidants or radical scavengers, preferred concentrations of which range from about 0.1% to about 10%, more preferably from about 1% to about 5%, by weight of the composition.

Non-limiting examples of anti-oxidants or radical scavengers for use herein include ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

E) Chelators

The skin benefit agent for use herein can also include chelating agents. As used herein, the term "chelating agent" or "chelator" refers to those skin benefit agents capable of removing a metal ion from a system by forming a complex so that the metal ion cannot readily participate in or catalyze chemical reactions.

The chelating agents as skin benefit agents for use herein are preferably formulated at concentrations ranging from about 0.1% to about 10%, more preferably from about 1% to about 5%, by weight of the composition. Non-limiting examples of suitable chelating agents are described in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995.

Preferred chelating agents for use in the active phase of the compositions of the present invention include furildioxime, furilmonoxime, and derivatives thereof.

F) Flavonoids

The skin benefit agent for use herein includes flavonoid compounds suitable for use on the hair or skin, preferred concentrations of which range from about 0.01% to about 20%, more preferably from about 0.1% to about 10%, more preferably from about 0.5% to about 5%, by weight of the composition.

Non-limiting examples of flavonoids compounds suitable for use as skin benefit agents include flavanones such as unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1-C8 alkyl, C1-C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Among these flavanoid compounds, preferred are unsubstituted flavanone, methoxy flavanones, unsubstituted chalcone, 2',4-dihydroxy chalcone, isoflavone, flavone, and mixtures thereof, more preferably soy isoflavones.

Other non-limiting examples of flavanoid compounds suitable for use as skin benefit agents herein are described in U.S. Pat. Nos. 5,686,082 and 5,686,367.

G) Anti-Inflammatory Agents

The skin benefit agent for use in the present composition can include anti-inflammatory agents, preferred concentrations of which range from about 0.1% to about 10%, more preferably from about 0.5% to about 5%, by weight of the composition.

Non-limiting examples of steroidal anti-inflammatory agents suitable for use herein include corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

Nonsteroidal anti-inflammatory agents are also suitable for use herein as skin benefit agents in the active phase of the compositions. Non-limiting examples of non-steroidal anti-inflammatory agents suitable for use herein include oxicams (e.g., piroxicam, isoxicam, tenoxicam, sudoxicam, CP-14, 304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac); fenamates (e.g., mefenamic, meclofenamic, flufenamic, niflumic, tolfenamic acids); propionic acid derivatives (e.g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof.

Other non-limiting examples of suitable anti-inflammatory or similar other skin benefit agents include candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, sea whip extract, and combinations thereof.

Other non-limiting examples of suitable anti-inflammatory or similar other skin benefit agents include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific non-limiting examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, disodium 3-succinyloxy-beta-glycyrrhetinate, and combinations thereof.

H) Anti-Cellulite Agents

The skin benefit agent for use in the compositions of the present invention anti-cellulite agents, non-limiting examples of which include xanthine compounds such as caffeine, theophylline, theobromine, aminophylline, and combinations thereof.

I) Topical Anesthetics

The skin benefit agent for use in the present invention include topical anesthetics, non-limiting examples of which include benzocaine, lidocaine, bupivacaine, chlorprocaine, dibucaine, etidocaine, mepivacaine, tetracaine, dyclonine, hexylcaine, procaine, ketamine, pramoxine, phenol, pharmaceutically acceptable salts thereof, and combinations thereof.

J) Tanning Actives

The skin benefit agent for use in the present invention include tanning actives, preferred concentrations of which range from about 0.1% to about 20% by weight of the composition. Non-limiting examples of such tanning agents include dihydroxyacetone, which is also known as DHA or 1,3-dihydroxy-2-propanone.

K) Skin Lightening Agents

The skin benefit agent for use in the present invention can include skin lightening agents, preferred concentrations of which range from about 0.1% to about 10%, more preferably from about 0.2% to about 5%, more preferably from about 0.5% to about 2%, by weight of the composition. Non-limiting examples of skin lightening agents suitable for use herein include kojic acid, arbutin, ascorbic acid and derivatives thereof (e.g., magnesium ascorbyl phosphate or sodium ascorbyl phosphate), and extracts (e.g., mulberry extract, placental extract) as well as titanium dioxide and zinc oxide. Non-limiting examples of skin lightening agents suitable for use herein also include those described in WO 95/34280, WO 95/07432, and WO 95/23780.

L) Skin Soothing and Skin Healing Actives

The skin benefit agent for use in the present invention include skin soothing and skin healing actives, preferred concentrations of which range from about 0.1% to about 30%, more preferably from about 0.5% to about 20%, still more preferably from about 0.5% to about 10%, by weight of the composition. Non-limiting examples of skin soothing or skin healing actives suitable for use herein include panthenoic acid derivatives (e.g., panthenol, dexpanthenol, ethyl panthenol), aloe vera, allantoin, bisabolol, and dipotassium glycyrrhizinate.

M) Antimicrobial Actives

The skin benefit agent for use in compositions of the present invention may include antimicrobial actives, preferred concentrations of which range from about 0.001% to about 10%, more preferably from about 0.01% to about 5%, and still more preferably from about 0.05% to about 2%, by weight of the compositions.

Non-limiting examples of antimicrobial actives for use herein includes β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione, clotrimazole, and combinations thereof.

N) Sunscreen Actives

The skin benefit agent for use in the present invention may comprise a sunscreen active, either organic or inorganic sunscreen actives. Among the inorganic sunscreens useful herein are metallic oxides such as titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof.

The concentration of the sunscreen active for use in the composition preferably ranges from about 0.1% to about 20%, more typically from about 0.5% to about 10%, by weight of the composition. Exact amounts of such sunscreen actives will vary depending upon the sunscreen or sunscreens chosen and the desired Sun Protection Factor (SPF).

A wide variety of conventional organic sunscreen actives are also suitable for use herein, non-limiting examples of which include p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane. Among these sunscreens, preferred are 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and combinations thereof.

Non-limiting examples of other sunscreen actives suitable for use herein include those described in U.S. Pat. No. 4,937, 370 issued to Sabatelli on Jun. 26, 1990, and U.S. Pat. No. 4,999,186 issued to Sabatelli & Spirnak on Mar. 12, 1991. Among those sunscreen actives described, preferred are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy) dibenzoylmethane and mixtures thereof. Especially preferred sunscreen actives include 4,4'-t-butylmethoxydibenzoylmethane, 2-ethylhexyl-p-methoxycinnamate, phenyl benzimidazole sulfonic acid, and octocrylene.

O) Visual Skin Enhancers

The skin benefit agent for use in compositions of the present invention may include visual skin enhancement ingredients. These include ingredients that mask the appearance of any number of skin imperfections such as age spot, fine lines, wrinkles, blemishes etc., including but not limited to titanium dioxide, zinc oxide and iron oxides. Also suitable for use herein are organic particulates that diffuse light when deposited on the skin. Preferred concentrations of these ingredients range from about 0.001% to about 10%, more preferably from about 0.01% to about 5%, and still more preferably from about 0.05% to about 2%, by weight of the compositions.

C. Hydrophobically Modified Non-platelet Particle

The rinsable personal care composition of the present invention comprises from 0.01 to 20 weight percent of a hydrophobically modified non-platelet particle. The non-platelet particles of the personal care compositions preferably comprises no more than about 20 weight percent of the composition, more preferably no more than about 10 weight percent, even more preferably no more than about 7 weight percent, and still more preferably no more than about 5 weight percent of the personal care composition. The non-platelet particles of the personal care composition preferably comprises at least about 0.01 weight percent of the personal care composition, more preferably at least about 0.05 weight percent, even more preferably at least about 0.1 weight percent, and still more preferably at least about 0.25 by weight of the composition.

Examples of particles which can be used in their hydrophobically modified state include but are not limited to those derived from a wide variety of materials including those derived from inorganic, organic, natural, and synthetic sources, provided that they meet the non-platelet shape requirement. Non-limiting examples of these materials include those selected from the group consisting of almond meal, alumina, aluminum oxide, titanium dioxide, sodium stearate, stearic acid, zinc stearate, aluminum silicate, apricot seed powder, aftapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are micronized particles made from mixed polymers (e.g., copolymers, terpolymers, etc.), such as polyethylene/polypropylene copolymer, polyethylene/propylene/isobutylene copolymer, polyethylene/styrene copolymer, and the like.

The particle size is determined by measuring the diameter thickness of the particulate material through traditional means such as light scattering. The non-platelet particle of the personal care compositions preferably have an average diameter not greater than about 200 µm, more preferably not greater than 100 µm, even more preferably not greater than about 80 µm, still more preferably not greater than about 60 µm. The non-platelet particle of the personal care compositions preferably have a diameter of at least about 0.01 µm, more preferably at least about 0.05 µm, even more preferably at least about 0.1 µm, and still more preferably at least about 0.2 µm.

When particles are applied and rinsed as described in the Particle Deposition Tape Strip Method (below), the deposited particle on the skin is at least 0.5 µg/cm$^2$, more preferably at least 1 µg/cm$^2$, and most preferably at least 5 µg/cm$^2$.

In an embodiment of the present invention the non-platelet particle is either hydrophobic or has been hydrophobically modified. The Particle Contact Angle Test of the present invention is used to determine contact angle of non-platelet particles. The greater the contact angle, the greater the hydrophobicity of the non-platelet particle. The non-platelet particle of the present invention possess a contact angle of at least 60°, more preferably greater than 80°, even more preferably greater than 100°, still more preferably greater than 110°, even still more preferably greater than 120°, even still even more preferably greater than 130°, even still even more preferably greater than 135°. The hydrophobically modified non-platelet particle or HMNPP allows for the entrapment of the HMNPP within the dispersed phase and greater deposition of the HMNPP. In a preferred embodiment of the present invention, the invention contains both HMNPPs and a dispersed oil phase. Preferably the ratio of HMNPP to skin benefit agent or emollient is 1:1 to about 1:100 more preferably 1:2 to about 1:80, still more preferably 1:3 to about 1:70 and most preferably 1:7 to about 1:60.

The HMNPP of the present invention preferably has a hydrophobic coating comprising no more than about 20 weight percent of the total particle weight, more preferably no more than about 15 weight percent, even more preferably no more than about 10 weight percent, even more preferably no more than 5 weight percent and even more preferably no more than 2 weight percent. The HMNPP of the present invention preferably has a hydrophobic coating comprising at least about 0.1 weight percent of the total particle weight, more preferably at least about 0.5 weight percent, even more preferably at least about 1 weight percent. Nonlimiting examples of the hydrophobic surface treatment useful herein include silicones, acrylate silicone copolymers, acrylate polymers, alkyl silane, isopropyl titanium triisostearate, sodium stearate, magnesium myristate, perfluoroalcohol phosphate, perfluoropolymethyl isopropyl ether, lecithin, carnauba wax, polyethylene, chitosan, lauroyl lysine, plant lipid extracts and mixtures thereof, preferably, silicones, silanes and stearates.

When formulated into a product, the HMNPP's are preferably entrapped within the skin benefit agent or emollient.

This necessitates that the oil phase particle size is generally larger than the HMNPP. In a preferred embodiment of the invention, the skin benefit agent or emollient contain only a small number of HMNPPs per oil particles. Preferably this is less than 20, more preferably less than 10, most preferably less than 5. These parameters, the relative size of the oil droplets to the HMNPP and the approximate number of HMNPP particles per dispersed oil particles, can be determined by using visual inspection with light microscopy.

The HMNPP and skin benefit agent or emollient can be mixed into the composition via a premix or separately. For the case of separate addition, the hydrophobic pigments partition into the skin benefit agent or emollient oil phase during the processing of the formulation. However, preferably the HMNPP may not be supplied dispersed in liquid prior to their incorporation into the personal care composition of the present invention.

D. Aqueous Phase

The composition will preferably contain an aquouse phase. The aqueous phase will be composed of water and/or other hydroxyl containing solvents such as glycerine, propylene glycol and other water miscible solvents. The aqueous phase may be continuous or discontinuous depending on the formulation. Preferably, the composition will contain at least 10% water, more preferably at least 20%, even more preferably at least 30% and even more preferably 40% and most preferably at least 50%. Preferably the aqueous phase will comprise no more than 90% of the composition, even more preferably no more than 80% of the composition, even more preferably less than 75% of the composition, and most preferably less than 70% of the composition.

E. Optional Ingredients

The compositions of the present invention may contain one or more additional skin care components. In a preferred embodiment, where the composition is to be in contact with human keratinous tissue, the additional components should be suitable for application to keratinous tissue, that is, when incorporated into the composition they are suitable for use in contact with human keratinous tissue without undue toxicity, incompatibility, instability, allergic response, and the like within the scope of sound medical judgment.

The *CTFA Cosmetic Ingredient Handbook*, Second Edition (1992) describes a wide variety of nonlimiting cosmetic and pharmaceutical ingredients commonly used in the personal care industry, which are suitable for use in the compositions of the present invention.

In any embodiment of the present invention, however, the additional components useful herein can be categorized by the benefit they provide or by their postulated mode of action. However, it is to be understood that the additional components useful herein can in some instances provide more than one benefit or operate via more than one mode of action. Therefore, classifications herein are made for the sake of convenience and are not intended to limit the active to that particular application or applications listed.

a. Particles

The present invention may optionally comprise particles having a wide range of shapes, surface characteristics, and hardness characteristics can be utilized to provide optical effect. These particles of the personal care compositions preferably have an average diameter not greater than about 200 µm, more preferably not greater than 100 µm, even more preferably not greater than about 80 µm, still more preferably not greater than than about 60 µm. The particles of the personal care compositions preferably have a diameter of at least about 0.01 µm, more preferably at least about 0.05 µm, even more preferably at least about 0.1 µm, and still more preferably at least about 0.2 µm.

These particles may be used as is, without being hydrophobically modified (although some may in fact be 'naturally hydrophobic'), include but are not limited to those derived from a wide variety of materials including those derived from inorganic, organic, natural, and synthetic sources. Non-limiting examples of these materials include those selected from the group consisting of almond meal, alumina, aluminum oxide, titanium dioxide, mica, coated mica, sodium stearate, stearic acid, zinc stearate, aluminum silicate, apricot seed powder, aftapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are micronized particles made from mixed polymers (e.g., copolymers, terpolymers, etc.), such as polyethylene/polypropylene copolymer, polyethylene/propylene/isobutylene copolymer, polyethylene/styrene copolymer, and the like.

b. Interference Pigments

The present invention may optionally comprise interference pigments, such as those disclosed in co-pending and commonly assigned under U.S. patent application Ser. No. 10/841,173 filed on May 7, 2004 by Clapp, et al.

The interference pigments of the present invention are platelet particulates. The platelet particulates of the personal care compositions preferably have a thickness of no more than about 51 µm, more preferably no more than about 2 µm, still more preferably no more than about 1 µm. The platelet particulates of the personal care composition preferably have a thickness of at least about 0.02 µm, more preferably at least about 0.05 µm, even more preferably at least about 0.1 µm, and still more preferably at least about 0.2 µm.

The interference pigment of the personal care compositions preferably have an average diameter not greater than about 200 µm, more preferably not greater than 100 µm, even more preferably not greater than about 80 µm, still more preferably not greater than than about 60 µm. The interference pigment of the personal care compositions preferably have a diameter of at least about 0.1 µm, more preferably at least about 1.0 µm, even more preferably at least about 2.0 µm, and still more preferably at least about 5.0 µm.

The interference pigment of the personal care compositions comprises a multilayer structure. The centre of the particulates is a flat substrate with a refractive index (RI) normally below 1.8. A wide variety of particle substrates are useful herein. Nonlimiting examples are natural mica, synthetic mica, graphite, talc, kaolin, alumina flake, bismuth oxychloride, silica flake, glass flake, ceramics, titanium dioxide, $CaSO_4$, $CaCO_3$, $BaSO_4$, borosilicate and mixtures thereof, preferably mica, silica and alumina flakes.

A layer of thin film or a multiple layer of thin films are coated on the surface of a substrate described above. The thin films are made of highly refractive materials. The refractive index of these materials is normally above 1.8.

A wide variety of thin films are useful herein. Nonlimiting examples are $TiO_2$, $Fe_2O_3$, $SnO_2$, $Cr_2O_3$, ZnO, ZnS, ZnO, SnO, $ZrO_2$, $CaF_2$, $Al_2O_3$, BiOCl, and mixtures thereof or in the form of separate layers, preferably $TiO_2$, $Fe_2O_3$, $Cr_2O_3SnO_2$. For the multiple layer structures, the thin films can be consisted of all high refractive index materials or alternation of thin films with high and low RI materials with the high RI film as the top layer.

The interference color is a function of the thickness of thin film, the thickness for a specific color may be different for different materials. For $TiO_2$, a layer of 40 nm to 60 nm or a whole number multiple thereof gives silver color, 60 nm to 80 nm yellow color, 80 nm to 100 nm red color, 100 nm to 130 nm blue color, 130 nm to 160 nm green color. In addition to the interference color, other transparent absorption pigments can be precipitated on top of or simultaneously with the $TiO_2$ layer. Common materials are red or black iron oxide, ferric ferrocyanide, chromium oxide or carmine. It was found that the color of the interference pigment in addition to its brightness had a significant influence on human perception of skin tone. In general, preferred colors are silver, gold, red, green and mixtures thereof.

Nonlimiting examples of the interference pigments useful herein include those supplied by Persperse, Inc. under the trade name PRESTIGE®, FLONAC®; supplied by EMD Chemicals, Inc. under the trade name TIMIRON®, COLORONA®, DICHRONA® and XIRONA®; and supplied by Kobo Products, Inc. under the trade name Kobopearl®; and supplied by Engelhard Co. under the trade name FLAMENCO®, TIMICA®, DUOCHROME®.

c. Hydrophobically Modified Interference Pigments

The present invention may optionally comprise Hydrophobically Modified Interference Pigments, such as those disclosed in co-pending and commonly assigned under U.S. patent application Ser. No. 10/841,173 filed on May 7, 2004 by Clapp, et al.

In an embodiment of the present invention the interference pigment surface is either hydrophobic or has been hydrophobically modified. The Particle Contact Angle Test of the present invention is used to determine contact angle of interference pigments. The greater the contact angle, the greater the hydrophobicity of the interference pigment. The interference pigment of the present invention possess a contact angle of at least 60°, more preferably greater than 80°, even more preferably greater than 100°, still more preferably greater than 110°, even still more preferably greater than 120°, even still even more preferably greater than 130°, even still even more preferably greater than 140°. The hydrophobically modified interference pigment or HMIP allows for the entrapment of the HMIP within the skin benefit agent or emollient and greater deposition of the HMIP.

When formulated into a product, the HMIP's are preferably entrapped within the the skin benefit agent or emollient.

The HMIP and the oil can be mixed into the composition via a premix or separately. For the case of separate addition, the hydrophobic pigments partition into the oil phase during the processing of the formulation. Nonlimiting examples of the hydrophobic surface treatment useful herein include silicones, acrylate silicone copolymers, acrylate polymers, alkyl silane, isopropyl titanium triisostearate, sodium stearate, magnesium myristate, perfluoroalcohol phosphate, perfluoropolymethyl isopropyl ether, lecithin, carnauba wax, polyethylene, chitosan, lauroyl lysine, plant lipid extracts and mixtures thereof, preferably, silicones, silanes and stearates. Surface treatment houses include US Cosmetics, KOBO Products Inc., and Cardre Inc.

d. Structurants

The present invention may optionally comprise a structurant. The structurant can provide the dispersed phase with the correct rheological properties. This can aid in providing effective deposition and retention to the skin, the structured oil or oil phase should have a viscosity in the range of 100 to about 200,000 poise measured at 1 Sec−1, preferably 200 to about 100,000 poise, and most preferably 200 to about 50,000 poise as determined using the lipid rheology method described below. The amount of structurant required to produce this viscosity will vary depending on the oil and the structurant, but in general, the structurant will preferably be less than 75 weight percent of the dispersed oil phase, more preferably less than 50 weight percent, and still more preferably less than 35 weight percent of the dispersed oil phase.

Structurants meeting the above requirements with the selected skin compatible oil can form 3-dimensional network to build up the viscosity of the selected oils. It has been found that such structured oil phases, i.e., built with the 3-dimensional network, are extremely desirable for use as wet-skin treatment compositions used in bathing. These structured oils can deposit and be retained very effectively on wet skin and retained after rinsing and drying to provide long-lasting after wash skin benefit without causing a too oily/greasy wet and dry feel. It is believed that the highly desirable in-use and after-use properties of such structured oils are due to their shear thinning rheological properties and the weak structure of the network. Due to its high low-shear viscosity, the 3-dimensional network structured oil can stick and retain well on the skin during application of the skin conditioner. After being deposited on the skin, the network yields easily during rubbing due to the weak structuring of the crystal network and its lower high-shear viscosity.

The structurant can be either an organic or inorganic structurant. Examples of organic thickeners suitable for the invention are solid fatty acid esters, natural or modified fats, fatty acid, fatty amine, fatty alcohol, natural and synthetic waxes, and petrolatum, and the block copolymers sold under the name KRATON by Shell. Inorganic structuring agents include hydrophobically modified silica or hydrophobically modified clay. Nonlimiting examples of inorganic structurants are BENTONE 27V, BENTONE 38V or BENTONE GEL MIO V from Rheox; and CAB-O-SIL TS720 or CAB-O-SIL M5 from Cabot Corporation.

The structurant may be crystalline may be a natural or synthetic crystalline wax. Mineral, animal or plant (vegetable) waxes are all described as natural waxes. Synthetic waxes are described as those waxes that have been synthetically polymerized from raw materials or chemically modified natural waxes.

Among the natural crystalline waxes which may be used are petroleum based waxes such as paraffins and microcrystalline wax. Molecular weights of paraffin waxes generally range from 360 to 420 (26 to 30 carbon atoms), although versions with longer chains (molecular weights up to 600) are available. Typical melting points are 126-134° F. (52-57° C.), the high molecular weight versions have melting points near 170° F. (77° C.). Paraffin waxes are brittle and the addition of oil weakens the structure (lowers the tensile strength).

Microcrystalline waxes (MC) melting points are 145 to 195° F. (63-91° C.). The crystals of MC wax are small and irregular and consist of several types: plates, malcrystalline and needle. Animal waxes can be obtained from such things as bees, insects or whales. These waxes include but are not limited to beeswax, Chinese wax, shellac wax, spermaceti and wool wax. Plant waxes can be derived from beans, leaves and berries. Plant or vegetable waxes can include bayberry, candelilla, carnauba, cotton, esparto, fir, Japan, ouricury, palm, rice-oil, sugar cane, ucuhuba and cocoa butter.

Among synthetic crystalline waxes which may be used are crystalline polymers such as polyethylene, Fischer-Tropsch waxes such as polymethylene, chemically modified waxes, polymerized alpha olefins and synthetic animal waxes. For example, siliconyl beeswax may be used which is beeswax that has been chemically modified.

Another structurant that may be optionally used in the present invention is the microcrystalline wax petrolatum (also known as petrolatum or mineral jelly), which typically comprises about 90% by wt. of a natural mixture of microcrystalline waxes plus minor amounts of other impurities In addition, structurant may be a natural or synthetic hydrogenated oil or fat. Hydrogenated oils are also commonly referred to as fats. In addition some fatty acids and fatty alcohols can be used as structurant as well as salts of fatty acids, hydroxy fatty acids and fatty acid esters.

Hydrogenated oils can be hydrogenated vegetable oils, hydrogenated coconut oil, hydrogenated palm kernel oil, hydrogenated rapeseed oil and many others. Another hydrogenated oil is castorwax.

Along with size and shape, a high concentration of particles is required so that the crystals interact in the dispersion. Above a certain critical volume fraction of crystals, these interactions will lead to a buildup of a network that extends throughout the whole volume. The crystal network creates a solid-like material having viscoelastic properties.

Thus, the ability of the fat crystals of the hydrogenated oils to form continuous networks that entrap the oil depends on the solid fat content in the fat/oil mixtures and also on crystal morphology. For example, when there is a high concentration of beta prime crystals, a continuous network of small crystals extends through the sample and the sample is solid and stable. Typically, at solid fat contents of 40-50%, the consistency is hard and brittle, at 20-30% the system is solid-like but yielding, at lower concentrations the consistency is more fluid often with a grainy texture and at very low concentrations the fat crystals separate from the liquid. However, the exact concentrations of crystals required to build desired structures varies depending on the fat and oil used. In practice, the crystal formation is also dependent on processing conditions such as temperature, crystal formation rate and shearing.

Crystalline long chain fatty acids and long chain fatty alcohols can also be used to structure benefit agents. Examples of fatty acids are myristic acid, palmitic acid, stearic acid, arachidic acid and behenic acid. Examples of fatty alcohols are palmityl alcohol, stearyl alcohol, arachyl alcohol and behenyl alcohol. Some crystalline fatty acid esters and glyceride esters will also provide structuring benefit.

In addition, the crystalline materials can be combined with other structuring materials such as natural and synthetic waxes to form composite networks to structure benefit agents e. Thickeners The compositions of the present invention, in some embodiments, may further include one or more thickening/aqueous phase stability agents. Because different stability agents thicken with different efficiencies, it is difficult to provide an accurate compositional range, however, when present, the composition preferably comprises no more than about 10 weight percent, more preferably no more than about 8 weight percent, and still more preferably no more than about 7 weight percent of the personal care composition. When present, the thickening/aqueous phase stability agent preferably comprises at least about 0.01 weight percent, more preferably at least about 0.05 weight percent, and still more preferably at least about 0.1 weight percent of the personal care composition.

Nonlimiting examples of thickening agents useful herein include carboxylic acid polymers such as the carbomers (such as those commercially available under the tradename CARBOPOL® 900 series from B.F. Goodrich; e.g., CARBOPOL® 954). Other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as CARBOPOL® 1342, CARBOPOL® 1382, PEMULEN TR-1, and PEMULEN TR-2, from B.F. Goodrich.

Other nonlimiting examples of thickening agents include crosslinked polyacrylate polymers including both cationic and nonionic polymers.

Still other nonlimiting examples of thickening agents include the polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500W, SSSA100H, from Lipo Chemicals, Inc., (Patterson, N.J.).

Another nonlimiting class of thickening agents useful herein are the polysaccharides. Nonlimiting examples of polysaccharide gelling agents include those selected from cellulose, and cellulose derivatives. Preferred among the alkyl hydroxyalkyl cellulose ethers is the material given the CTFA designation cetyl hydroxyethylcellulose, which is the ether of cetyl alcohol and hydroxyethylcellulose, sold under the tradename NATROSEL® CS PLUS from Aqualon Corporation (Wilmington, Del.). Other useful polysaccharides include scleroglucans which are a linear chain of (1-3) linked glucose units with a (1-6) linked glucose every three units, a commercially available example of which is CLEAROGEL™ CS11 from Michel Mercier Products Inc. (Mountainside, N.J.).

Another nonlimiting class of thickening agents useful herein are the gums. Nonlimiting examples of gums useful herein include hectorite, hydrated silica, xantham gum, and mixtures thereof.

Yet another nonlimiting class of thickening agents useful herein are the modified starches. Acrylate modified starches such as WATERLOCK® from Grain Processing Corporation may be used. Hydroxypropyl starch phosphate, tradename STRUCTURE XL from National Starch is another example of a useful modified starch, and other useful examples include ARISTOFLEX HMB (Ammonium Acrylodimethyltaruate/ Beheneth-25 Methacrylate Crosspolymer) from Clariant and cationic stabylens.

f. Cationic Polymers

The present invention may also contain organic cationic deposition polymer Concentrations of the cationic deposition polymer preferably range from about 0.025% to about 3%, more preferably from about 0.05% to about 2%, even more preferably from about 0.1% to about 1%, by weight of the personal care composition.

F. Analytical Methods:

a. Lipid Rheology Test

Lipid rheology is measured on a TA Instruments AR2000 stress-controlled rheometer with a Peltier temperature controlled sample stage or an equivalent. A parallel plate geometry is used with a 40 mm plate and a 1 mm gap. The lower plate is heated to 85° C. and the melted lipid and structurant (if present) is added onto the lower plate and allowed to equilibrate. The upper plate is then lowered to the 1 mm gap while ensuring the lipid fills the gap fully, [spinning the top plate and adding more lipid to promote wicking], and the sample is cooled quickly to 25° C. and equilibrated at 25° C. for 5 minutes. Viscosity is then measured using a stress-ramp procedure common on these types of machines using a logarithmic stress ramp from 20 to 2000 Pa at a rate of 60 seconds per decade (2 minute ramp test), with 20 measurements points per decade. The starting and ending stress is sufficient to induce flow and reach a shear rate of at least 10 sec-1. Viscosity is recorded and the data fitted to a power law model using Equation 1. Only points between 0.001 sec–1 and 40 seconds-1 are to be used in the power law fit. The viscosity at 1.0 sec–1 is calculated from Equation 1. One should carefully watch the sample during the test so that when the material is ejected from under the plate, the method is stopped.

Viscosities are recorded and the data fit to a power law with the following Equation 1:

$$\eta = \kappa \cdot \gamma(dot)^{(n-1)}$$

where $\eta$=viscosity, $\kappa$ is the consistency and $\gamma(dot)$ is the shear rate, and n is the shear index.

The viscosity at 1 sec–1 is then calculated using the calculated values of $\eta$ and n from the fitted data.

b. HMNPP Deposition Tape Strip Method

The Pigment Deposition Tape Strip Method can be used to semi-quantitatively determine deposition of shiny particles onto keratinous surfaces. The method employs the use of a tape strip for removing particles from skin and imaging these particles for a quantitation of deposited particles.

The first step is to weigh 1 g of pigment that is the same as those in the product being tested in a vial. Next, 9 g melted petrolatum is added and mixed well with a spatula.

Weigh out 994.17 g purified water (Millipore or equivalent). While mixing @~600-700 rpm using a Lightning Laboratory Stirrer or Heidolph 2051 mixer and appropriate blade, to the water slowly add 3.50 g Pemulen TR-1 (BF Goodrich) so as to prevent clumping. Follow this with 30 minutes of stirring to ensure complete hydration of Pemulen. To the mixture, while still stirring slowly, add 2.33 g TEA (Triethanolamine 99%-Dow Chemical). Follow this by an additional 30 minutes of stirring to ensure homogeneity.

Evaluate product for separation after standing for 1 hour. Separation is not acceptable. Store in glass jars at room temperature. Now, mix 1 ml of the pigment/petrolatum mixture with 19 ml of 0.35% Pemulen Gel mixture, using Cito Unguator on speed 8 (~2050 rpm) for 4 minutes. This combination of the 1 ml of the pigment/petrolatum mixture with 19 ml of 0.35% Pemulen Gel mixture will be used to evaluate deposition of pigment on the skin.

Wash inner arms of subject with Olay Sensitive Skin bar and warm water, rinsing until all soap has been removed. Dry with clean paper towels. Mark inner arms of subject with three 4×6 cm sites per arm. Apply to site #1 (upper left, nearest elbow) 5 µl of the mixture described previously, spreading evenly over site and rubbing in with gloved finger for ~20 seconds covering entire site. This application equals 1 µg pigment per cm$^2$. Apply to site #2 (middle left) 24 µl of mixture described previously, spreading evenly over site and rubbing in with gloved finger for ~20 seconds covering entire site. This application equals 5 µg pigment per cm$^2$. Apply to site #3 (bottom left, nearest wrist) 48 µl of mixture described previously. This equals 10 µg per cm$^2$. Apply to site #4 (top right, nearest elbow) 96 µl of mixture described previously. This equals 20 µg per cm$^2$. Let sites air dry for a minimum of 10 min. Apply to site #5 (middle right) 96 µl of the product being tested. Apply to site #6 (bottom right, nearest wrist) 96 µl of the product being tested. Rinse each site #5 and #6 with warm tap water for 10 seconds each, not contaminating one site with the next while rinsing. Then pat each site dry gently with clean paper towels, again not contaminating one site with the next.

Take approximately 1" of Scotch Tape and apply to site #1. Rub over the top of the applied tape to pick up product below. Remove the tape and reapply same tape to very same previously stripped area, so as to pull product from area twice on the same tape. Then secure this stripping tape to a clean microscope slide, product side up, marking the slide as "1 µg/cm$^2$". Repeat the application of Scotch Tape method described previously for sites #2 through #6 (in that order), marking each slide appropriately.

Take microscope images of each tape strip that are made with a 10× objective and top lighting.

Visually compare the numbers of pigment particles in sites #5 and #6 images with those in the standard sites #1 through #4 images and give a deposition level, for example, 8 g/cm$^2$. Take an average of the observations of sites #5 and #6 from at least 3 people.

c. Particle Contact Angle Test

The Particle Contact Angle Test is used to determine hydrophobicity of shiny particles. The greater the contact angle the greater the hydrophobicity of the particle.

A Spectra-Tech Qwik Handi-Press (Thermo Nicolet, Madison, Wis.) is used to compress the powder into 7-mm diameter discs. After applying firm hand pressure, the compression is held for 1 min prior to releasing pressure and removing the disc. The disc is examined for smoothness and rejected unless the surface is smooth. First Ten Angstrom FTÅ 200 (First Ten Angstrom, Portsmouth, Va.) contact angle analyzer is employed to determine advancing and receding contact angles. 7 microliters of water (Millipore, Milli Q deionized, distilled) is dangled from the needle and slowly placed on the middle of the disc. The needle is left inserted in the drop but not in contact with disc. 0.1 microliters/second of water is pumped into the drop. Contact angle images were captured every 0.1 sec. until the maximum contact angle is obtained. The process is reversed to determine the receding contact angle in that the needle is left in the drop and fluid is removed at 0.1 microliters/second until the minimum contact angle is obtained. Images were obtained at 0.1 images/second, then calculate the contact angle. To calculate the contact angle, a curve is fitted to the profile of the drop on both sides of the drop. The baseline is drawn across the drop. The intersection of the curves and baseline is determined on both sides of the drop. The tangent (slopes) of the curve at the intersection is determined on both sides of the drop. The contact angle is the angle between the baseline and the tangent interior to the drop. The average contact angle is determined from the contact angles from both sides of the drop.

d. Lather Volume

Lather volume of a personal care composition can be measured using a graduated cylinder and a tumbling apparatus. A 1,000 ml graduated cylinder is chosen which is marked in 10 ml increments and has a height of 14.5 inches at the 1,000 ml mark from the inside of its base (for example, Pyrex No. 2982). Distilled water (100 grams at 23° C.) is added to the graduated cylinder. The cylinder is clamped in a rotating device, which clamps the cylinder with an axis of rotation that transects the center of the graduated cylinder. One gram of the total personal care composition is added into the graduated cylinder and the cylinder is capped. The cylinder is rotated at a rate of 10 revolutions in about 20 seconds, and stopped in a vertical position to complete the first rotation sequence. A timer is set to allow 30 seconds for the lather thus generated to drain. After 30 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum foam height is 1,000 ml (even if the total foam height exceeds the 1,000 ml mark on the graduated cylinder). One minute after the first rotation is completed, a second rotation sequence is commenced which is identical in speed and duration to the first rotation sequence. The second lather volume is recorded in the same manner as the first, after the same 30 seconds of drainage time. A third sequence is completed and the third lather volume is measured in the same manner, with the same pause between each for drainage and taking the measurement.

The lather result after each sequence is added together and the Total Lather Volume determined as the sum of the three measurements, in ml. The Flash Lather Volume is the result after the first rotation sequence only, in ml, i.e., the first lather volume.

G. EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

| Ingredient | Ex. 1 wt % | Ex. 2 wt % | Ex. 3 wt % | Ex. 4 wt % | Ex. 5 wt % | Ex. 6 wt % |
|---|---|---|---|---|---|---|
| I. Aqueous Phase Composition | | | | | | |
| Polymer | | | | | | |
| Structure XL (Hydroxypropyl Starch Phosphate from National Starch) | | | | | | |
| Pemulen TR2 (Acrylates/C10-30 Alkyl Acrylate Crosspolymer from Noveon, Inc.) | | | 0.3 | | 0.5 | |
| Carbopol Ultrez 10 (Carbomer from Noveon, Inc.) | | 1.5 | | 1.8 | | |
| Xanthan Gum | | | | 0.1 | | |
| Sepigel 305 (Polyacrylamide and C13-14 Isoparaffin and Laureth-7 from Seppic) | 3.0 | | | | | 2.7 |
| Surfactant | | | | | | |
| Polawax (Emulsifying Wax NF from Croda) | | | | | | 2.5 |
| PEG-100 Stearate | | | | | | |
| Tween 80 (Polysorbate 80 from Uniqema Americas) | 2.1 | | 0.25 | 0.3 | | |
| Ammonium Lauryl Sulfate | | | | | | |
| Incroquat Behenyl TMS (Behenetrimonium methosulfate and cetearyl alcohole from Croda) | | 2.0 | | | 2.5 | |
| Additional Ingredients | | | | | | |
| NHance 3196 (Guar Hydroxypropyl Trimonium Chloride from Aqualon) | | | | | 0.15 | |
| PEG 14M | | | | | | 0.1 |
| AMP-95 (Amino Methyl Propanol from Angus Chemical) | | 0.1 | 0.14 | 0.1 | 0.18 | |
| Glycerine | 0.6 | | 0.5 | | | 0.7 |
| Salicylic Acid | | | | | | |

-continued

| Ingredient | Ex. 1 wt % | Ex. 2 wt % | Ex. 3 wt % | Ex. 4 wt % | Ex. 5 wt % | Ex. 6 wt % |
|---|---|---|---|---|---|---|
| Fragrance | 1.0 | 1.0 | 1.0 | 1.0 | 1.0 | 1.0 |
| Preservatives | 0.8 | 0.8 | 0.8 | 0.8 | 0.8 | 0.8 |
| Water | Q.S. | Q.S. | Q.S. | Q.S. | Q.S. | Q.S. |
| II. Lipid/HMIP phase Composition | | | | | | |
| Superwhite Protopet (Petrolatum from WITCO) | 4 | | 17.5 | 20 | | |
| Hydrobrite 1000 PO (Mineral Oil from WITCO) | | | | | | 15 |
| Dow Corning 200 Fluid 50 cst (Dimethicone Fluid from Dow Corning) | | 2 | | 2 | 3 | |
| Isopropyl Palmitate | 1 | | | | | |
| Soybean Oil | | 18 | | | | 4 |
| Puresyn 101LT (Polydecene from Exxon Mobile) | | | | 3 | | |
| Lipovol Sun (Sunflower Seed Oil from Lipo) | 12 | | | | 11 | |
| SAT-T-CR50 (Titanium Dioxide/Siloxane from US Cosmetics) | 1.75 | | | | | |
| Cardre LDP 1000 (Polymethyl methacrylate/titanium dioxide/triethoxycaprylylsilane from LCW) | | | | | | |
| Cardre LDP 2000 (Polymethyl Methacrylate/Zinc Oxide/Dimethicone from LCW) | | 1 | | | | |
| Cardre Titanium Dioxide AS (titanium dioxide/alkyl silane from LCW) | | | 0.4 | | | |
| BTD-TTS2 (Titanium Dioxide/Isopropyl Titanium Triisostearate/Triethoxycaprylylsilane) | | | | | | 0.8 |
| SAT-R-77491 (Red Iron oxide/Dimethylpolysiloxane from US Cosmetics) | 0.4 | | | | | |
| DHL-Y-77492 (Yellow Iron oxide/Diemthylpolysiloxane from US Cosmetics) | 0.3 | | | | | |
| SAT-B-77499 (Black Iron oxide/Diemthylpolysiloxane from US Cosmetics) | 0.14 | | | | | |
| 73044 Cardre Titanium Dioxide/PMMA AQ (titanium dioxide/polymethylmethacrylate/dimethicone copolyol from LCW) | | | | | | |
| RBTD-11S2 (titanium dioxide/triethoxy caprylylsilane from Kobo Products Inc.) | | | | 5 | | |
| RBTD-I2 (Titanium Dioxide/isopropyl titanium triisostearate from Kobo Products Inc.) | | | | | 2.5 | |
| Kobopearl Stellar White-11S2 (Mica/Titanium Dioxide/Triethoxy caprylylsilane from Kobo Products Inc.) | | | | | | |
| SAT-Timiron Splendid Red (Titanium Dioxide/Mica/Silica/Dimethicone from US Cosmetics) | | | | | | 0.2 |
| Kobopearl Fine White-11S2 (Mica/Titanium Dioxide//Triethoxy caprylylsilane from Kobo Products Inc.) | | | | | 1 | |
| SAT-Timiron Super Green(Mica/Titanium Dioxide/Dimethicone from US Cosmetics) | | | | | | |
| SA-M-M (Mica/Dimethicone from US Cosmetics) | | | | 0.5 | | |
| SAT-Flamenco Ultra Silk 2500 (Mica/Titanium Dioxide/Dimethicone from US Cosmetics) | | | | | | |
| TiPure R101-1 (Titanium dioxide from Dupont) | 2 | | | | | 0.5 |
| BTD-11S2 (Titanium Dioxide/Triethoxy caprylylsilane from Kobo Products, Inc.) | | | | | | |
| Polyacrylate-4 (Helicone HC Maple from Kobo Products, Inc.) | | | | | | |

Examples 1-6

Premix the lipid phase and the hydrophobically modified particles and heat to 55° C. If the formula contains a polymer, such as Nhance 3196 and PEG 14M from the above examples, add it to the water first, mix well. Add Polymer phase to the water in a stainless steel vessel using an overhead mixer, allow the polymer to fully incorporate. pH adjust if needed. Add Surfactant phase, mix and heat to 80° C. Add lipid premix mix well until batch is homogeneous in appearance. Allow batch to cool to 38° C. If the formula contains the following: perfume, preservatives, salicylic acid, glycerine and non modified titanium dioxide, add it with additional mixing.

| Ingredient | Ex. 7 wt % | Ex. 8 wt % | Ex. 9 wt % | Ex. 10 wt % | Ex. 11 wt % | Ex. 12 wt % |
|---|---|---|---|---|---|---|
| I. Aqueous Phase Composition | | | | | | |
| Polymer | | | | | | |
| Structure XL (Hydroxypropyl Starch Phosphate from National Starch) | 3.5 | | 3.5 | 3.5 | 4 | 3 |
| Pemulen TR2 (Acrylates/C10-30 Alkyl Acrylate Crosspolymer from Noveon, Inc.) | | | | | | |
| Carbopol Ultrez 10 (Carbomer from Noveon, Inc.) | | | | | | |
| Xanthan Gum | | 0.8 | | | | |
| Sepigel 305 (Polyacrylamide and C13-14 Isoparaffin and Laureth-7 from Seppic) | | | | | | |
| Surfactant | | | | | | |
| Polawax (Emulsifying Wax NF from Croda) | 2.0 | | 2.0 | | | |
| PEG-100 Stearate | | 2 | | | | 1 |
| Tween 80 (Polysorbate 80 from Uniqema Americas) | | | | | | 0.1 |
| Ammonium Lauryl Sulfate | | | | | 2.5 | |
| Incroquat Behenyl TMS (Behenetrimonium methosulfate and cetearyl alcohole from Croda) | | | | 2.25 | | |
| Additional Ingredients | | | | | | |
| NHance 3196 (Guar Hydroxypropyl Trimonium Chloride from Aqualon) | | | | | | |
| PEG 14M | | | | | | |
| AMP-95 (Amino Methyl Propanol from Angus Chemical) | | | | | | |
| Glycerine | | 1 | | | 0.5 | |
| Salicylic Acid | | 0.1 | | | | |
| Fragrance | 1.0 | 1.0 | 1.0 | 1.0 | 1.0 | 1.0 |
| Preservatives | 0.8 | 0.8 | 0.8 | 0.8 | 0.8 | 0.8 |
| Water | Q.S. | Q.S. | Q.S. | Q.S. | Q.S. | Q.S. |
| II. Lipid/HMIP phase Composition | | | | | | |
| Superwhite Protopet (Petrolatum from WITCO) | 20 | 9 | 25 | 12 | 15 | 15 |
| Hydrobrite 1000 PO (Mineral Oil from WITCO) | | | | | 2 | |
| Dow Corning 200 Fluid 50 cst (Dimethicone Fluid from Dow Corning) | 2 | | 2 | | | |
| Isopropyl Palmitate | | 1 | | | | 3 |
| Soybean Oil | | | | | 5 | |
| Puresyn 101LT (Polydecene from Exxon Mobile) | | | | 2 | | |
| Lipovol Sun (Sunflower Seed Oil from Lipo) | | | | 4 | | |
| SAT-T-CR50 (Titanium Dioxide/Siloxane from US Cosmetics) | | | | | | |
| Cardre LDP 1000 (Polymethyl methacrylate/titanium dioxide/triethoxycaprylylsilane from LCW) | | 1.2 | | | | |
| Cardre LDP 2000 (Polymethyl Methacrylate/Zinc Oxide/Dimethicone from LCW) | | | | | | 0.7 |
| Cardre Titanium Dioxide AS (titanium dioxide/alkyl silane from LCW) | | | | | 0.5 | |
| BTD-TTS2 (Titanium Dioxide/Isopropyl Titanium Triisostearate/Triethoxycaprylylsilane) | | | | | | |

| Ingredient | Ex. 7 wt % | Ex. 8 wt % | Ex. 9 wt % | Ex. 10 wt % | Ex. 11 wt % | Ex. 12 wt % |
|---|---|---|---|---|---|---|
| SAT-R-77491 (Red Iron oxide/Dimethylpolysiloxane from US Cosmetics) | | | | | | |
| DHL-Y-77492 (Yellow Iron oxide/Diemthylpolysiloxane from US Cosmetics) | | | | | | |
| SAT-B-77499 (Black Iron oxide/Diemthylpolysiloxane from US Cosmetics) | | | | | | |
| 73044 Cardre Titanium Dioxide/PMMA AQ (titanium dioxide/polymethylmethacrylate/dimethicone copolyol from LCW) | | | | | | |
| RBTD-11S2 (titanium dioxide/triethoxy caprylylsilane from Kobo Products Inc.) | | | | | | |
| RBTD-I2 (Titanium Dioxide/isopropyl titanium triisostearate from Kobo Products Inc.) | | | | | | |
| Kobopearl Stellar White-11S2 (Mica/Titanium Dioxide/Triethoxy caprylylsilane from Kobo Products Inc.) | | | | 0.1 | | |
| SAT-Timiron Splendid Red (Titanium Dioxide/Mica/Silica/Dimethicone from US Cosmetics) | | | | | | |
| Kobopearl Fine White-11S2 (Mica/Titanium Dioxide//Triethoxy caprylylsilane from Kobo Products Inc.) | | 0.5 | | | | |
| SAT-Timiron Super Green(Mica/Titanium Dioxide/Dimethicone from US Cosmetics) | | | | | 0.2 | |
| SA-M-M (Mica/Dimethicone from US Cosmetics) | | | | | | |
| SAT-Flamenco Ultra Silk 2500 (Mica/Titanium Dioxide/Dimethicone from US Cosmetics) | | | 0.1 | | | |
| TiPure R101-1 (Titanium dioxide from Dupont) | | | | | 1.5 | |
| BTD-11S2 (Titanium Dioxide/Triethoxy caprylylsilane from Kobo Products, Inc.) | 1 | 0.4 | | | | |
| Polyacrylate-4 (Helicone HC Maple from Kobo Products, Inc.) | | | 0.2 | | | |

Examples 7-12

In a stainless steel vessel add lipid (at 50° C.) and hydrophobically modified particle and heat to 80° C. with mixing. Add polymer and allow to mix well. Add surfactant, allow to incorporate fully. Separately, heat water to 75° C. Add 75° C. water to lipid mixture and mix well until batch is homogeneous in appearance. Allow batch to cool to 38° C. If the formula contains the following: perfume, preservatives, salicylic acid, glycerine and non modified titanium dioxide, add it with additional mixing.

| Ingredient | Ex. 13 wt % | Ex. 14 wt % | Ex. 15 wt % | Ex. 16 wt % | Ex. 17 wt % |
|---|---|---|---|---|---|
| I. Aqueous Phase Composition | | | | | |
| Ammonium Laureth Sulfate | 9.4 | 12.5 | | | |
| Sodium Lauroamphoacetate | 3.9 | 5.3 | 2 | | 3.2 |
| Ammonium Lauryl Sulfate | 3.0 | 8.2 | | 7.4 | |
| Sodium Laureth Sulfate | | | 9 | 2.8 | 6.8 |
| Lauric Acid | 1.6 | 1 | | 0.5 | 0.7 |
| Mirataine CAB (Cocamidopropyl Betaine from Rhodia Inc.) | | | 1.6 | 5 | 3.2 |
| Trihydroxystearin | 1 | 0.7 | | 1.5 | 1 |
| N-Hance 3196 (Guar Hydroxypropyl Trimonium Chloride from Aqualon) | 0.7 | | | | |
| PEG 14M | 0.1 | 0.3 | 0.1 | 0.1 | 0.2 |
| Sodium Chloride | 0.7 | 2 | 3 | | 1 |

-continued

| Ingredient | Ex. 13 wt % | Ex. 14 wt % | Ex. 15 wt % | Ex. 16 wt % | Ex. 17 wt % |
|---|---|---|---|---|---|
| Citric Acid | | | 0.2 | 0.1 | 0.2 |
| Salicylic Acid | | | | | |
| Fragrance | 1.0 | 1.0 | 1.0 | 1.0 | 1.0 |
| Preservatives | 0.8 | 0.8 | 0.8 | 0.8 | 0.8 |
| Water | Q.S. | Q.S. | Q.S. | Q.S. | Q.S. |
| II. Lipid/HMIP phase Composition | | | | | |
| Superwhite Prototpet (Petrolatum from WITCO) | 17.5 | 20 | | | 15 |
| Hydrobrite 1000 PO (Mineral Oil from WITCO) | | | 15 | | |
| Dow Corning 200 Fluid 50 cst (Dimethicone Fluid from Dow Corning) | | 2 | | 3 | |
| Isopropyl Palmitate | | | | | 3 |
| Soybean Oil | | | 4 | | |
| Puresyn 101LT (Polydecene from Exxon Mobile) | | 3 | | | |
| Lipovol Sun (Sunflower Seed Oil from Lipo) | | | | 11 | |
| Cardre LDP 1000 (Polymethyl methacrylate/titanium dioxide/triethoxycaprylylsilane from LCW) | | | | 1 | |
| Cardre LDP 3000 (Polymethyl methacrylate/silica/triethoxycaprylylsilane from LCW) | 1 | | | | |
| Cardre Titanium Dioxide AS (titanium dioxide/alkyl silane from LCW) | | | | | 1 |
| SAT-Timiron MP115 Starluster (Mica/Titanium Dioxide/Dimethicone from US Cosmetics) | | 0.5 | | | |
| BTD-401 (Titanium Dioxide/Isopropyl Titanium Triisostearate from Kobo Products Inc.) | | | 2 | | |
| Kobopearl Fine White-11S10 (Mica/Titanium Dioxide//Triethoxy caprylylsilane from Kobo Products Inc.) | | | | 0.5 | |
| SAT-Timiron Super Green (Mica/Titanium Dioxide/Dimethicone from US Cosmetics) | | 0.1 | | | |
| SAT-Flamenco Ultra Silk (Mica/Titanium Dioxide/Dimethicone from US Cosmetics) | | | | 0.3 | |
| TiPure R101-01 (Titanium Dioxide from Dupont) | 2 | 1 | | 1.5 | |

Examples 13-17

The compositions described above is prepared by conventional formulation and mixing techniques. The aqueous phase ingredients are mixed in a stainless steel vessel using an overhead mixer and heated to 95° C. Add the trihydroxystearin and allow to fully incorporate into the mixture, then add preservatives. Allow the phase to cool with mixing. Premix the lipid phase and the hydrophobically modified particles and heat to 55° C. Once the aqueous phase has cooled to 31° C., the lipid/particle premix is added and mixed well until batch is homogeneous in appearance. If the formula contains a non modified particle, such as TiPure R101-01 from the above example, add it at this point to the mixing batch. Then add perfume. Keep agitation until a homogenous solution forms.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rinsable personal care composition comprising:
   a) 0.1 to 75 weight percent of a composition surfactant;
   b) 0.01 to 99 weight percent of a skin benefit agent or emollient;
   c) 0.01 to 20 weight percent of a hydrophobically modified non-platelet particle comprising:
      i. an average particle size not greater than about 80 μm;
      ii. an aspect ratio defined by A/B=or >0.20, wherein said length of said hydrophobically modified non-platelet particle being A and said width of said hydrophobically modified non-platelet particle being B;
      iii. a hydrophobic coating comprising no more than 20 weight percent of said hydrophobically modified non-platelet particle, wherein said hydrophobic coating comprises a material selected from the group consisting of silicone, acrylate silicone copolymers, alkyl silane, dimethicone, triethoxycaprysilane, dimethylpolysiloxane, and mixtures thereof; and
   d) 10 to 99 weight percent of water;
   wherein said composition comprises a ratio of said hydrophobically modified non-platelet particle to said skin benefit agent or emollient of about 1:7 to about 1:60.

2. The composition of claim 1, comprising 0.1 to 20 weight percent of said hydrophobically modified non-platelet particle.

3. The composition of claim 1, comprising 0.01 to no more than 1 weight percent of said hydrophobically non-platelet particle.

4. The composition of claim 1, comprising 0.01 to no more than 5 weight percent of said hydrophobically non-platelet particle.

5. The composition of claim 1, comprising 0.01 to no more than 80 weight percent of said skin benefit agent or emollient.

6. The composition of claim 1, comprising 1 to 99 weight percent of said skin benefit agent or emollient.

7. The composition of claim 1, wherein said skin benefit agent or emollient is selected from the group consisting of petrolatum, mineral oil, silicone, triglycerides, esters and mixtures thereof.

8. The composition of claim 1, wherein said composition comprises 0.1 to no more than 15 weight percent of said surfactant.

9. The composition of claim 8, wherein said composition surfactant is present in a gel-network.

10. The composition of claim 1, wherein said composition comprises at least 5 to 75 weight percent of a surfactant.

11. The composition of claim 10, wherein said composition comprises at least one anionic surfactant.

12. The composition of claim 10, further comprising a polymer.

13. The composition of claim 1, further comprising a structurant.

14. The composition of claim 1, further comprising a hydrophobically modified interference pigment.

15. The composition of claim 1, further comprising a particle.

16. The composition of claim 1, wherein said hydrophobic coating comprises silane.

17. The composition of claim 1, wherein said hydrophobic coating comprises dimethicone.

18. The composition of claim 1, wherein said hydrophobically modified non-platelet particle comprises titanium dioxide.

19. The composition of claim 1, wherein said hydrophobic coating comprises no more than 10 weight percent of said hydrophobically modified non-platelet particle.

20. A rinsable personal care composition comprising:
 a) 0.1 to 15 weight percent of a composition surfactant;
 b) 1 to 99 weight percent of a skin benefit agent or emollient;
 c) 0.1 to 20 weight percent of a hydrophobically modified non-platelet particle comprising:
  i. an average particle size from about 0.1 µm to about 80 µm;
  ii. an aspect ratio defined by A/B=or >0.20, wherein said length of said hydrophobically modified non-platelet particle being A and said width of said hydrophobically modified non-platelet particle being B;
  iii. a hydrophobic coating comprising no more than 10 weight percent of said hydrophobically modified non-platelet particle;
  iv. a contact angle of at least 60°; and
 d) 10 to 99 weight percent of water;
 wherein said composition comprises a ratio of said hydrophobically modified non-platelet particle to said skin benefit agent or emollient of about 1:7 to about 1:60.

21. The composition of claim 20, wherein at least 0.5 µg/cm$^2$ of said hydrophobically modified non-platelet particle is deposited on skin when said composition is rinsed off said skin.

22. The composition of claim 20, wherein said hydrophobic coating comprises a material selected from the group consisting of silicone, acrylate silicone copolymers, alkyl silane, dimethicone, triethoxycaprysilane, dimethylpolysiloxane, and mixtures thereof.

23. The composition of claim 20, wherein said hydrophobically modified non-platelet particle comprises titanium dioxide.

* * * * *